United States Patent [19]
Venham

[11] Patent Number: 5,280,100
[45] Date of Patent: Jan. 18, 1994

[54] METHYLAMYLKETOXIME BLOCKED POLYISOCYANATES AND THEIR USE IN HIGH SOLIDS COATINGS COMPOSITIONS

[75] Inventor: Lanny D. Venham, Paden City, W. Va.

[73] Assignee: Miles Inc., Pittsburgh, Pa.

[21] Appl. No.: 875,890

[22] Filed: Apr. 29, 1992

[51] Int. Cl.⁵ ............................................. C08G 18/81
[52] U.S. Cl. .................................... 528/45; 528/44; 528/52; 564/331; 564/333; 564/335
[58] Field of Search ............................ 528/45, 44, 52; 564/331, 333, 335

[56] References Cited

U.S. PATENT DOCUMENTS

| | | | |
|---|---|---|---|
| 4,486,556 | 12/1984 | Kordomenos et al. | 523/400 |
| 4,596,744 | 6/1986 | Anderson et al. | 428/418 |
| 4,708,995 | 11/1987 | Kordomenos et al. | 525/450 |
| 4,794,154 | 12/1988 | Benefiel | 528/45 |
| 4,808,658 | 2/1989 | Walz et al. | 524/591 |
| 4,847,346 | 7/1989 | Vorwerk et al. | 528/45 |
| 4,925,885 | 5/1990 | Rosthauser et al. | 528/45 |

*Primary Examiner*—John Kight, III
*Assistant Examiner*—Duc Truong
*Attorney, Agent, or Firm*—Joseph C. Gil; Thomas W. Roy

[57] ABSTRACT

The present invention relates to blocked polyisocyanates based on the reaction product of i) an organic polyisocyanate comprising a member selected from the group consisting of bis-(4-isocyanatocyclohexyl)-methane, NCO prepolymers prepared from bis-(4-isocyanatocyclohexyl)-methane, polyisocyanate adducts prepared from bis-(4-isocyanatocyclohexyl)-methane, isocyanurate group-containing polyisocyanates prepared from 1,6-hexamethylene diisocyanate and isocyanurate and allophanate group-containing polyisocyanates prepared from 1,6-hexamethylene diisocyanate with ii) methylamyl ketoxime.

6 Claims, No Drawings

METHYLAMYLKETOXIME BLOCKED POLYISOCYANATES AND THEIR USE IN HIGH SOLIDS COATINGS COMPOSITIONS

BACKGROUND OF THE INVENTION

1. Field of the Invention

The present invention relates to methylamylketoxime (MAKO) blocked polyisocyanates, which have a significantly reduced viscosity when compared to corresponding polyisocyanates blocked with methylethylketoxime (MEKO), and to the use of these polyisocyanates in high solids coating compositions.

2. Description of the Prior Art

In view of the increasing number of regulations requiring a reduction in the amount of volatile organic solvents present in coating compositions, many attempts have been made to formulate high solids coating compositions. One possibility is to optimize the selection of solvents or blends of solvents to determine those which provide the greatest reduction in viscosity based on the weight of the solvent. Another possibility is to formulate the coating compositions with lower viscosity raw materials.

Coating compositions based on a blocked polyisocyanate component and a polyol component are known. The purpose of the blocking agent prevents the polyisocyanate component from reacting with the polyol component prematurely. An advantage of these coating compositions over those based on fully reacted polyurethanes is that the viscosity of the individual components is less than the viscosity of the fully reacted polyurethane. During subsequent curing of the coating composition at elevated temperatures the blocking agent is released and the polyisocyanate and polyol components react to form a high molecular weight polyurethane.

One of the preferred classes of blocking agents are the oximes. These blocking agents provide the good storage stability which is generally associated with caprolactam blocking agents, yet release the blocking agent at much lower temperatures than those needed for caprolactam blocking agents. By good storage stability it is meant that the blocking agents prevent a premature reaction from occurring between isocyanate groups and hydroxyl groups which would increase the viscosity and possibly gel the coating composition.

Even though coating compositions based on oxime-blocked polyisocyanates and a polyol component have a lower viscosity than fully reacted polyurethanes, it is an object of the present invention to further reduce the viscosity of these systems without affecting the properties of the coatings obtained therefrom.

These objectives may be achieved in accordance with the present invention by using methylamyl ketoxime (MAKO) as the blocking agent for the polyisocyanate component. Certain polyisocyanates blocked with MAKO possess lower viscosities when compared to the same polyisocyanates blocked with methylethyl ketoxime (MEKO).

U.S. Pat. Nos. 4,486,556 and 4,708,995 are representative of a series of patents relating to electrodeposition coatings. Both of these patents describe the preparation of blocked polyisocyanates by blocking a biuret group-containing polyisocyanate based on 1,6-hexamethylene diisocyanate and an isocyanurate group-containing polyisocyanate based on toluene diisocyanate with MAKO. U.S. Pat. No. 4,847,346 describes the preparation of an MAKO-blocked polyisocyanate adduct wherein the adduct is prepared by reacting toluene diisocyanate with trimethylol propane. U.S. Pat. No. 4,808,658 describes the preparation of a polyisocyanate adduct blocked with 2-octanone oxime wherein the adduct is prepared by reacting isophorone diisocyanate with trimethylol propane. U.S. Pat. No. 4,794,154 describes the preparation of an MAKO-blocked polyisocyanate adduct wherein the adduct is prepared by reacting α, α, α',α'-tetramethyl-xylylene diisocyanate with trimethylol propane.

U.S. Pat. No. 4,596,744 is directed to the use of oximes containing at least 7 carbon atoms, preferably MAKO, as blocking agents. The preferred polyisocyanates are adducts prepared by reacting toluene diisocyanate with trimethylol propane and isocyanurate group-containing polyisocyanates based on 1,6-hexamethylene diisocyanate. However, in view of the fact that neither of these polyisocyanate adducts was blocked with MAKO in the examples of this reference, there is no recognition of the improvement in viscosity which may be obtained when the specific polyisocyanates of the present invention are blocked with MAKO.

SUMMARY OF THE INVENTION

The present invention relates to blocked polyisocyanates based on the reaction product of i) an organic polyisocyanate comprising a member selected from the group consisting of bis-(4-isocyanatocyclohexyl)-methane, NCO prepolymers prepared from bis-(4-isocyanatocyclohexyl)-methane, polyisocyanate adducts prepared from bis-(4-isocyanatocyclohexyl)-methane, isocyanurate group-containing polyisocyanates prepared from 1,6-hexamethylene diisocyanate and isocyanurate and allophanate group-containing polyisocyanates prepared from 1,6-hexamethylene diisocyanate with ii) methylamyl ketoxime.

DETAILED DESCRIPTION OF THE INVENTION

Suitable starting materials for the preparation of the blocked polyisocyanates according to the present invention include bis-(4-isocyanatocyclohexyl)-methane monomer, NCO prepolymers prepared from bis-(4-isocyanatocyclohexyl)-methane monomer and polyisocyanates adducts based on bis-(4-isocyanatocyclohexyl)-methane monomer. Polyisocyanate adducts are compounds containing free isocyanate groups and also carbodiimide groups, urethane groups, allophanate groups, isocyanurate groups, uretdione groups and/or biuret groups. Also suitable as starting materials are isocyanurate group-containing polyisocyanates based on HDI and isocyanurate and allophanate group-containing polyisocyanates based on HDI.

In accordance with the present invention the two previously named diisocyanates, i.e., bis-(4-isocyanatocyclohexyl)-methane and HDI, may be blended with other known diisocyanates or polyisocyanates before, during or after the preparation of the blocked polyisocyanates or before, during or after the preparation of the NCO prepolymers or polyisocyanate adducts. The other known diisocyanates or polyisocyanates may be used in amounts of up to about 75 mole percent, preferably up to about 40 mole percent, based on the total moles of the final product.

The NCO prepolymers which are suitable for use as starting materials according to the present invention are prepared by reacting an excess of bis-(4-isocyanatocyclohexyl)-methane with organic compounds containing at least two isocyanate-reactive groups by methods which are known in the art. The organic compounds can be divided into two groups, i.e., high molecular weight compounds having a molecular weight of 400 to about 6,000, preferably 800 to about 3,000, and low molecular weight compounds having a molecular weight below 400. The molecular weights are number average molecular weights ($M_n$) and are determined by end group analysis (OH number). Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and polyhydroxy polycarbonates are preferred.

Both the high and low molecular weight organic compounds are known and disclosed in U.S. Pat. No. 4,701,480, the disclosure of which is herein incorporated by reference.

Suitable polyisocyanate adducts prepared from bis-(4-isocyanatocyclohexyl)-methane or mixtures containing this diisocyanate as previously set forth include:

1) Isocyanurate group-containing polyisocyanates which may be prepared as set forth in DE-PS 2,616,416, EP-OS 3,765, EP-OS 10,589, EP-OS 47,452, US-PS 4,288,586 and US-PS 4,324,879. The isocyanato-isocyanurates generally have an average NCO functionality of 3 to 3.5 and an NCO content of 5 to 30%, preferably 10 to 25% and most preferably 15 to 25% by weight.

2) Uretdione diisocyanates which may be used as the sole component for preparing blocked polyisocyanates or which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906,126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 3 to 3.5.

4) Urethane group-containing polyisocyanates which may be prepared in accordance with the process disclosed in U.S. Pat. No. 3,183,112 by reacting excess quantities of bis-(4-isocyanatocyclohexyl)-methane with the previously described low molecular weight polyols, preferably trimethylol propane, glycerine, 1,2-dihydroxy propane or mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318 and 4,160,080; British Patent No. 994,890; and German Offenlegungsschrift 2,040,645. The allophanate group-containing polyisocyanates have a most preferred NCO content of 12 to 20% by weight and an (average) NCO functionality of 2.5 to 3.

6) Isocyanurate and allophanate group-containing polyisocyanates which may be prepared in accordance with the processes set forth in copending applications, U.S. Ser. Nos. 07/644,174 now U.S. Pat. No. 5,124,427; 733,549 now abandoned; 733,566 now abandoned; and 771,086, now abandoned, the disclosures of which are herein incorporated by reference.

7) Carbodiimide group-containing polyisocyanates which may be prepared by oligomerizing bis-(4-isocyanatocyclohexyl)-methane in the presence of known carbodiimidization catalysts.

The isocyanurate group-containing and the isocyanurate and allophanate group-containing polyisocyanates prepared from 1,6-hexamethylene diisocyanate or mixtures containing this diisocyanate as previously set forth may be prepared using the procedures set forth above for the preparation of these polyisocyanates from bis-(4-isocyanatocyclohexyl)-methane.

The reaction between the polyisocyanates and MAKO is generally conducted at or above room temperature, preferably from 40° to 80° C. and more preferably 50° to 70° C., optionally in the presence of a catalyst which catalyzes the reaction between isocyanate groups and the blocking agent such as a tin catalyst. However, due to the exothermic nature of the reaction a catalyst is generally not necessary. Preferably, the reaction mixture is cooled to maintain the temperature within the previously disclosed ranges. It is also possible in accordance with the invention to blend MAKO with other known blocking agents for isocyanate groups.

A solvent or solvent mixture may be used during the production of the blocked polyisocyanates. When a solvent is employed, the solvent or solvent mixture preferably remains in the composition until it is used. However, it is of course also possible to use a solvent simply to promote thorough mixing of the compounds used for preparing the blocked polyisocyanates and subsequently to distill off this solvent under vacuum leaving a ready-to-use mixture in solvent-free form which may be redissolved in solvents at any later stage.

Suitable solvents include the known polyurethane solvents such as toluene, xylene, butyl acetate, ethyl acetate, ethylene glycol monoethyl ether acetate, ethylene glycol monomethyl ether acetate, ethylene glycol monobutyl ether acetate, diethylene glycol monoethyl ether acetate, diethylene glycol monomethyl ether acetate, diethylene glycol monobutyl ether acetate, propylene glycol monomethyl ether acetate, methyl ethyl ketone or methyl isobutyl ketone, hydrocarbon solvents such as hexane and heptane, aromatic solvents and also mixtures of these solvents.

The use of solvents is not necessary for the blocked polyisocyanates according to the present invention because of the low viscosity of these polyisocyanates. However, the viscosity of the blocked polyisocyanates may be reduced by the addition of a solvent, e.g., when necessary for a particular application. Generally the solids content of the blocked polyisocyanates is greater than 20% and may be as high as 100%.

The blocked polyisocyanates according to the present invention may be present in admixture with other blocked polyisocyanates. These mixtures may be prepared by blending the monomeric diisocyanates to be used in accordance with the present invention with other monomeric diisocyanates or polyisocyanates as previously discussed. It is also possible to mix other NCO prepolymers and/or polyisocyanate adducts with those previously described for use in accordance with the invention either before, during or after the blocking reaction. These other polyisocyanates they may be blocked with MAKO and/or other known blocking agents.

The blocked polyisocyanates according to the present invention may be used in any application in which blocked polyisocyantes have previously been used. The blocked polyisocyanates are generally used as crosslinking agents for compounds containing isocyanate-reactive groups such as those previously set forth for preparing the prepolymers based on bis-(4-isocyanatocyclohexyl)-methane. The polyester polyols, polyether polyols, polyhydroxy polyacrylates and polyhydroxy polycarbonates are preferred.

The invention is further illustrated but is not intended to be limited by the following examples in which all parts and percentages are by weight unless otherwise specified.

EXAMPLES

The blocked isocyanate contents and equivalent weights are based on the total weight of the composition.

EXAMPLE 1

Preparation of an NCO prepolymer

A round bottom flask was charged with bis-(4-isocyanatocyclohexyl)-methane (2093.3 g, 15.96 eq), a polyester diol (999.6 g, 1.18 eq) prepared from adipic acid, hexane diol and neopentyl glycol (molar ratio of diols 65:35), trimethyl-pentanediol (170.5 g, 3.57 eq), and a mixture of aromatic hydrocarbon solvents, (Aromatic 100, 735.0 g). This mixture was stirred and heated to 60° C. under a nitrogen blanket. Catalyst (dibutyltin dilaurate, 1.49 g) was added and the temperature was raised to 90° C. and maintained there for 8 to 10 hours. The final isocyanate content was slightly below the theoretical value of 13.07%.

EXAMPLE 2

(Comparison) Preparation of an MEKO blocked NCO prepolymer

A round bottom flask was charged with the NCO prepolymer solution from Example 1 (1000.0 g, 3.01 eq) and methoxypropylacetate (183.75 g). To this stirred solution was slowly added methylethyl ketoxime (265.0 g, 3.04 eq), while cooling the flask with a water bath. The temperature was not allowed to exceed 80° C. After the addition was complete, the mixture was stirred for 1 to 2 hours until the isocyanate content was below 0.1%. The product had a viscosity of 3,900 mPa.s at 25° C., a solids content of 75%, a blocked isocyanate content of 8.73%, and an equivalent weight of 481.1.

EXAMPLE 3

Preparation of an MAKO blocked NCO prepolymer

A round bottom flask was charged with the NCO prepolymer solution from Example 1 (950.0 g, 2.86 eq) and methoxypropylacetate (174.56 g). To this stirred solution was slowly added methylamyl ketoxime (372.8 g, 2.89 eq), while cooling the flask with a water bath. The temperature was not allowed to exceed 80° C. After the addition was complete, the mixture was stirred for 1 to 2 hours until the isocyanate content was below 0.1%. The product had a viscosity of 2,940 mPa.s at 25° C., a solids content of 76.7%, a blocked isocyanate content of 8.03%, and an equivalent weight of 523.0.

EXAMPLE 4

(Comparison) Preparation of MEKO blocked bis-(4-isocyanatocyclohexyl)-methane

A round bottom flask was charged with bis-(4-isocyanatocyclohexyl)-methane (54.06 g, 0.4121 eq) and xylene (10.0 g). To this stirred solution was slowly added methylethyl ketoxime (35.94 g, 0.4126 eq), while cooling the flask with a water bath. The temperature was not allowed to exceed 80° C. After the addition was complete, the mixture was stirred for 1 to 2 hours until the isocyanate content was below 0.2% (usually below 0.1%). The product had a viscosity of 25,000 mPa.s at 40° C., a solids content of 90.0%, a blocked isocyanate content of 17.3%, and an equivalent weight of 242.6.

EXAMPLE 5

Preparation of MAKO blocked bis-(4-isocyanatocyclohexyl)-methane

A round bottom flask was charged with bis-(4-isocyanatocyclohexyl)-methane (45.33 g, 0.3456 eq) and xylene (10.0 g). To this stirred solution was slowly added methylamyl ketoxime (44.64 g, 0.3460 eq), while cooling the flask with a water bath. The temperature was not allowed to exceed 80° C. After the addition was complete, the mixture was stirred for 1 to 2 hours until the isocyanate content was below 0.2% (usually below 0.1%). The product had a viscosity of 2,540 mPa.s at 40° C., a solids content of 90.0%, a blocked isocyanate content of 14.5%, and an equivalent weight of 289.2 g/eq.

EXAMPLE 6

Preparation of partially trimerized bis-(4-isocyanatocyclohexyl)-methane

A round bottom flask was charged with bis-(4-isocyanatocyclohexyl) methane (750.0 g, 5.72 eq) and xylene (83.3 g). A nitrogen inlet tube was placed into the solution and a slow stream of nitrogen was bubbled through for two hours. The solution was heated to 70° C. and catalyst solution (4.0 g) was added. The catalyst solution was prepared by mixing 47.2 g of a 40%, benzyltrimethylammonium hydroxide solution in methanol with 59.9 g of 1-butanol. The temperature increased from the exothermic reaction. The temperature was maintained between 90° and 100° C. for approximately 2 hours until an isocyanate content (determined by titration) of 18.7% was obtained. Di-(2-ethylhexylphosphate (1.55 g) was then added to inactivate the catalyst. The product had a viscosity of 32,000 mPa.s at 28° C., an isocyanate content of 18.7%, and an equivalent weight of 224.6.

EXAMPLE 7

(Comparison) Preparation of MEKO blocked, partially trimerized bis-(4-isocyanatocyclohexyl)-methane A round bottom flask was charged with the partially trimerized bis-(4-isocyanatocyclohexyl)-methane of Example 6 (200.0 g, 0.89 eq) and methoxypropylacetate (64.56 g). To this stirred solution was slowly added methylethyl ketoxime (78.25 g, 0.90 eq), while cooling the flask with a water bath. The temperature was not allowed to exceed 80° C. After the addition was complete, the mixture was stirred for 1 to 2 hours until the isocyanate content was 0.03%. The product had a viscosity of 117,200 mPa.s at 25° C., a solids content of 75.3%, a blocked isocyanate content of 10.9%, and an equivalent weight of 385.3.

EXAMPLE 8

Preparation of MAKO blocked, partially trimerized bis-(4-isocyanatocyclohexyl)-methane A round bottom flask was charged with the partially trimerized bis-(4-isocyanatocyclohexyl)-methane of Example 6 (200.0 g, 0.89 eq) and methoxypropylacetate (76.92 g). To this stirred solution was slowly added methylamyl ketoxime (115.96 g, 0.90 eq), while cooling the flask with a water bath. The temperature was not allowed to exceed 80° C. After the addition was complete, the mixture was stirred for 1 to 2 hours until the isocyanate content was 0.06%. The product had a viscosity of 18,500 mPa.s at 25° C., a solids content of 75%, a blocked isocyanate content of 9.5%, and an equivalent weight of 441.4.

EXAMPLE 9

Preparation of a polyisocyanate adduct containing isocyanurate and allophanate groups To a 500 ml 3-neck flask equipped with a gas bubbler, mechanical stirrer, thermometer and condenser was added 3017 g of 1,6-hexamethylene diisocyanate and 133 g of 1-butanol. The stirred mixture was heated for 1 hour at 60° C. while dry nitrogen was bubbled through the reaction mixture. The temperature of the urethane reaction mixture was then raised to 90° C. To the reaction mixture at 90° C. was added 2.14 g (30 ppm) of a catalyst solution. The catalyst solution was a 4.4% solution of benzyltrimethylammonium hydroxide in 2-butanol. When the reaction mixutre reached an NCO content of 34.8%, the reaction was stopped by adding 2.14 g (30 ppm) of di-(2-ethylhexyl) phosphate. The excess monomer was removed by thin film evaporation to provide an almost colorless clear liquid having a viscosity of 630 mPa.s (25° C.), an NCO content of 19.7% and a free monomer (HDI) content of 0.35%. The yield was 48.6%.

EXAMPLE 10

(Comparison) Preparation of an MEKO blocked polyisocyanate adduct containing isocyanurate and allophanate groups A round bottom flask was charged with the polyisocyanate adduct of Example 9 (1000.0 g, 4.31 eq), xylene (229.8 g), and methoxypropylacetate (229.8 g). To this stirred solution was slowly added methylethyl ketoxime (382.7 g, 4.39 eq), while cooling the flask with a water bath. The temperature did not exceed 60° C. After the addition was complete, the mixture was stirred for 1 to 2 hours until the isocyanate content was 0.24%. The product had a viscosity of 840 mPa.s at 25° C., a solids content of 75.0%, a blocked isocyanate content of 9.84%, and an equivalent weight of 427.0.

EXAMPLE 11

Preparation of MAKO blocked polyisocyanate adduct containing isocyanurate and allophanate groups A round bottom flask was charged with the polyisocyanate adduct of Example 9 (500.0 g, 2.16 eq), xylene (130.12 g), and methoxypropylacetate (130.12 g). To this stirred solution was slowly added methylamyl ketoxime (283.8 g, 2.2 eq), while cooling the flask with a water bath. The temperature did not exceed 60° C. After the addition was complete, the mixture was stirred for 1 to 2 hours until the isocyanate content was 0.18%. The product had a viscosity of 600 mPa.s at 25° C., a solids content of 75.0%, a blocked isocyanate content of 8.69%, and an equivalent weight of 483.1.

EXAMPLE 12

(Comparison) Preparation of MEKO blocked isocyanurate group-containing polyisocyanate A round bottom flask was charged with the isocyanurate group-containing polyisocyanate (750.0 g, 3.87 eq), and Aromatic 100 (363.3 g). The isocyanurate group-containing polyisocyanate was prepared by trimerizing a portion of the isocyanate groups of 1,6-hexamethylene diisocyanate, contained tris-(6-isocyanatohexyl)-isocyanurate and higher homologs thereof and had an isocyanate content of 21.6% by weight, a content of monomeric diisocyanate of <0.2%, a viscosity at 20° C. of 3,000 mPa.s and an average isocyanate functionality of about 3.3. To this stirred solution was slowly added methylethyl ketoxime (340.0 g, 3.90 eq), while cooling the flask with a water bath. The temperature did not exceed 70° C. After the addition was complete, the mixture was stirred for 1 to 2 hours until the isocyanate content was 0.01%. The product had a viscosity of 3230 mPa.s at 25° C., a solids content of 75.0%, a blocked isocyanate content of 11.2%, and an equivalent weight of 375.0.

EXAMPLE 13

Preparation of MAKO blocked isocyanurate group-containing polyisocyanate

A round bottom flask was charged with the isocyanurate group-containing polyisocyanate described in Example 12 (750.0 g, 3.87 eq) and Aromatic 100 (417.9 g). To this stirred solution was slowly added methylamyl ketoxime (518.7 g, 4.02 eq), while cooling the flask with a water bath. The temperature did not exceed 70° C. After the addition was complete, the mixture was stirred for 1 to 2 hours until the isocyanate content was 0.07%. The product had a viscosity of 1084 mPa.s at 25° C., a solids content of 75.0%, a blocked isocyanate content of 9.6%, and an equivalent weight of 437.5.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A blocked polyisocyanate comprising the reaction product of
    i) an organic polyisocyanate comprising a member selected from the group consisting of bis-(4-isocyanatocyclohexyl)-methane, NCO prepolymers prepared from bis-(4-isocyanatocyclohexyl)-methane, polyisocyanate adducts prepared from bis-(4-isocyanatocyclohexyl)-methane, isocyanurate group-containing polyisocyanates prepared from 1,6-hexamethylene diisocyanate and isocyanurate and allophanate group-containing polyisocyanates prepared from 1,6-hexamethylene diisocyanate with
    ii) methylamyl ketoxime.

2. The blocked polyisocyanate of claim 1 wherein said organic polyisocyanate comprises bis-(4-isocyanatocyclohexyl)-methane.

3. The blocked polyisocyanate of claim 1 wherein said organic polyisocyanate comprises an NCO prepolymer prepared from bis-(4-isocyanatocyclohexyl)-methane.

4. The blocked polyisocyanate of claim 1 wherein said organic polyisocyanate comprises a polyisocyanate adduct prepared from bis-(4-isocyanatocyclohexyl)-methane.

5. The blocked polyisocyanate of claim 1 wherein said organic polyisocyanate comprises an isocyanurate group-containing polyisocyanate prepared from 1,6-hexamethylene diisocyanate.

6. The blocked polyisocyanate of claim 1 wherein said organic polyisocyanate comprises an isocyanurate and allophanate group-containing polyisocyanate prepared from 1,6-hexamethylene diisocyanate.

* * * * *